(12) United States Patent
Shin

(10) Patent No.: US 7,270,637 B2
(45) Date of Patent: Sep. 18, 2007

(54) DEVICE FOR AND METHOD OF MEASURING BLOOD FLOW USING BIO-PHOTON EMISSION

(75) Inventor: Sang-hoon Shin, Seongnam-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 258 days.

(21) Appl. No.: 10/921,972

(22) Filed: Aug. 20, 2004

(65) Prior Publication Data

US 2005/0154316 A1    Jul. 14, 2005

(30) Foreign Application Priority Data

Jan. 12, 2004  (KR) .................. 10-2004-0002031

(51) Int. Cl.
*A61B 5/02* (2006.01)
(52) U.S. Cl. ............ 600/504; 600/407; 600/436; 600/476; 600/481; 600/500
(58) Field of Classification Search ............... 600/409, 600/500, 501, 504, 300, 301, 407, 436, 476, 600/481
See application file for complete search history.

(56) References Cited

U.S. PATENT DOCUMENTS

| | | | | |
|---|---|---|---|---|
| 5,212,667 | A | * | 5/1993 | Tomlinson et al. ............ 367/7 |
| 5,656,807 | A | * | 8/1997 | Packard ................. 250/214 VT |
| 5,866,907 | A | * | 2/1999 | Drukier et al. ............ 250/366 |
| 5,954,658 | A | * | 9/1999 | Gorti .......................... 600/504 |
| 6,055,450 | A | * | 4/2000 | Ashburn .................... 600/431 |

FOREIGN PATENT DOCUMENTS

| | | |
|---|---|---|
| EP | 0 984 268 | 3/2000 |
| EP | 1 126 271 | 8/2001 |

OTHER PUBLICATIONS

Kobayashi, et al., "In vivo imaging of spontaneous ultraweak photon emission from a rat's brain correlated with cerebral energy metabolism and oxidative stress", Neuroscience Research 34(2):103-113 (Jul. 1999).
[Author unknown], Biophotons, Master's Thesis of Seoul National University, (Feb. 2003) [(Copyright 2002) by Seoul National University Library (http://library.snu.ac.kr)] English Abstract appears on page 39.
Cohen, et al. "Biophoton emission of the human body", Indian J. of Experimental Biology, vol. 41(5), pp. 440-445 (May 2003).
Kim, et al., "Biophoton Emission from Fingernails and Fingerprints of Living Human Subjects", Acupuncture & Electro-Therapeutics Res. Int. J., vol. 27(2), pp. 85-94, (2002).
Kobayashi, et al., "In vivo imaging of spontaneous ultraweak photon emission from a rat's brain correlated with cerebral energy metabolism and oxidative stress", Neuroscience Research, vol. 34(2), pp.103-113, (Jul. 1999).

* cited by examiner

*Primary Examiner*—Charles A. Marmor
*Assistant Examiner*—Zoe E Baxter
(74) *Attorney, Agent, or Firm*—Lee & Morse, P.C.

(57) ABSTRACT

A device for and a method of measuring a blood flow of a living body having blood vessels that emit bio-photons and through which blood flows, the device including a detector positioned adjacent to a predetermined portion of the living body for measuring a bio-photon emission from the living body and a processor for analyzing and displaying the blood flow of the living body based on a value of the bio-photon emission.

8 Claims, 2 Drawing Sheets

DEVICE FOR AND METHOD OF MEASURING BLOOD FLOW USING BIO-PHOTON EMISSION

BACKGROUND OF THE INVENTION

1. Field of the Invention

The present invention relates to a device for and method of measuring blood flow. More particularly, the present invention relates to a device for and method of measuring blood flow using bio-photon emission.

2. Description of the Related Art

Cardiovascular diseases (CVDs), along with cancers, are regarded as the most life threatening illnesses to modern human beings. Among CVDs, a cerebral apoplexy, i.e., a stroke, occurs when, due to hardening of the arteries and cholesterol collected on the walls of blood vessels in the brain, the blood vessels become narrow or clogged. Thrombus may be produced in portions of a body, such as the heart and its adjacent organs, where the arteries are hardening. In addition, mental stress reduces the amount of blood that flows into the heart, thus resulting in a high probability of death from heart disease.

Generally, death from heart disease most likely occurs in patients whose coronary arteries, which send blood to the heart, narrow by 50% in at least one portion of the coronary arteries or who have already had one or more heart attacks.

An ischemic stroke can be categorized into two types, a complete ischemic stroke or a partial ischemic stroke depending on how blood circulation disorder is affected. In a case of a complete ischemic stroke, blood circulation in a portion of the brain is completely cut off, and a cerebral infarction occurs. Since a cerebral infarction makes the portion of the brain in which it occurs functionally irrecoverable, disorders due to the cerebral infarction are permanent.

A transient ischemic attack (TIA) is transient and includes local neurological symptoms due to a transient reduction of the blood supply to the brain. A TIA causes symptoms similar to a stroke, but differs from the stroke in that the TIA is only a temporary disease. In particular, a TIA may last for several minutes and then disappear. A TIA is a warning signal that a patient might have a stroke later due to dysfunctional blood circulation in the brain.

A conventional method of measuring an amount or rate of blood flow can be categorized into a method using the Doppler effect and a method using electromagnetic induction. Further, the method using the Doppler effect is classified into a method using a laser and a method using ultrasonic waves. When a laser Doppler blood flowmeter is used, the rate of blood that flows through blood vessels is measured by inserting a glass fiber into a blood vessel and irradiating a laser beam in the blood vessel. Then, the rate of blood is measured using a variation of wavelength of a reflected light. When an ultrasonic blood flowmeter is used, blood flow is measured using a variation of an ultrasonic wave that is externally applied to blood. A fundamental principle of the ultrasonic blood flowmeter is the same as that of the laser Doppler blood flowmeter. An electromagnetic blood flowmeter measures the amount or rate of blood flow by detecting an electromotive force (EMF) of blood generated after a magnetic field is applied to blood vessels.

Disadvantageously, measurement results of blood flow using the aforementioned conventional blood flowmeters are not precise because signals are affected by a stimulus to a human body or tissues inside or outside the skin. In addition, because these blood flowmeters are bulky, they are quite difficult to use, install, or transport.

SUMMARY OF THE INVENTION

The present invention is therefore directed to a device for and method of measuring blood flow using bio-photon emission, which substantially overcome one or more of the problems due to the limitations and disadvantages of the related art.

It is a feature of an embodiment of the present invention to provide a device for and method of measuring blood flow using bio-photon emission that are economical and relatively simple.

It is another feature of an embodiment of the present invention to provide a device for and method of measuring blood flow using bio-photon emission that provide real time measurements to a patient being examined.

It is another feature of an embodiment of the present invention to provide a device for and method of measuring blood flow using bio-photon emission that are able to be connected to various communication devices to enable remote treatment and accumulation of information.

At least one of the above features and other advantages may be provided by a device for measuring a blood flow of a living body having blood vessels that emit bio-photons and through which blood flows, the device including a detector positioned adjacent to a predetermined portion of the living body for measuring a bio-photon emission from the living body and a processor for analyzing and displaying the blood flow of the living body based on a value of the bio-photon emission.

The device may further include a shutter for controlling an amount of light incident on the detector. The detector may operate in a darkroom. The detector may be a photomultiplier or an optical receiver.

The device may further include a power supply for supplying power to the detector, a conveyor operable to move the detector three-dimensionally, and a preamplifier for converting the bio-photon emission detected by the detector into an electric signal and amplifying the electric signal.

The conveyor may include a stand, a support fixed on the stand, and a convey arm attached to the support operable to three-dimensionally control the movement of the detector.

The processor may include a display unit. The device may further include a communication device for transmitting results of the analysis of the bio-photon emission.

At least one of the above features and other advantages may be provided by a method of measuring a blood flow of a living body having blood vessels that emit bio-photons and through which blood flows, the method including measuring a bio-photon emission using a detector, converting the bio-photon emission into an electric signal and amplifying the electric signal, calculating an amount of bio-photon emission measure per unit of time $I_D$ based on the amplified electric signal, comparing the amount of bio-photon emission per unit time $I_D$ with a preset value, and displaying a result of the comparison.

Comparing the amount of bio-photon emission per unit time $I_D$ with the preset value may be performed using the following inequality:

$$\left|\frac{I_D - I_{ref}}{I_{ref}}\right| \times 100 \geq I_{th},$$

wherein $I_{ref}$ is an average of amounts of bio-photon emissions measured on the living body for several previous days and $I_{th}$ is the preset value.

The method may further include issuing a warning signal to the user if $$\left|\frac{I_D - I_{ref}}{I_{ref}}\right| \times 100$$

is greater than or equal to the preset value $I_{th}$.

Measuring the bio-photon emission may include positioning the detector adjacent to a predetermined portion of the living body, opening a shutter on the detector, and receiving the bio-photon emission by the detector.

Measuring the bio-photon emission may be performed in a darkroom.

The method may further include transmitting the result of the comparison using a communication device.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Korean Patent Application No. 2004-02031, filed on Jan. 12, 2004, in the Korean Intellectual Property Office, and entitled: "Device for and Method of Measuring Blood Flow Using Bio-Photon Emission," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
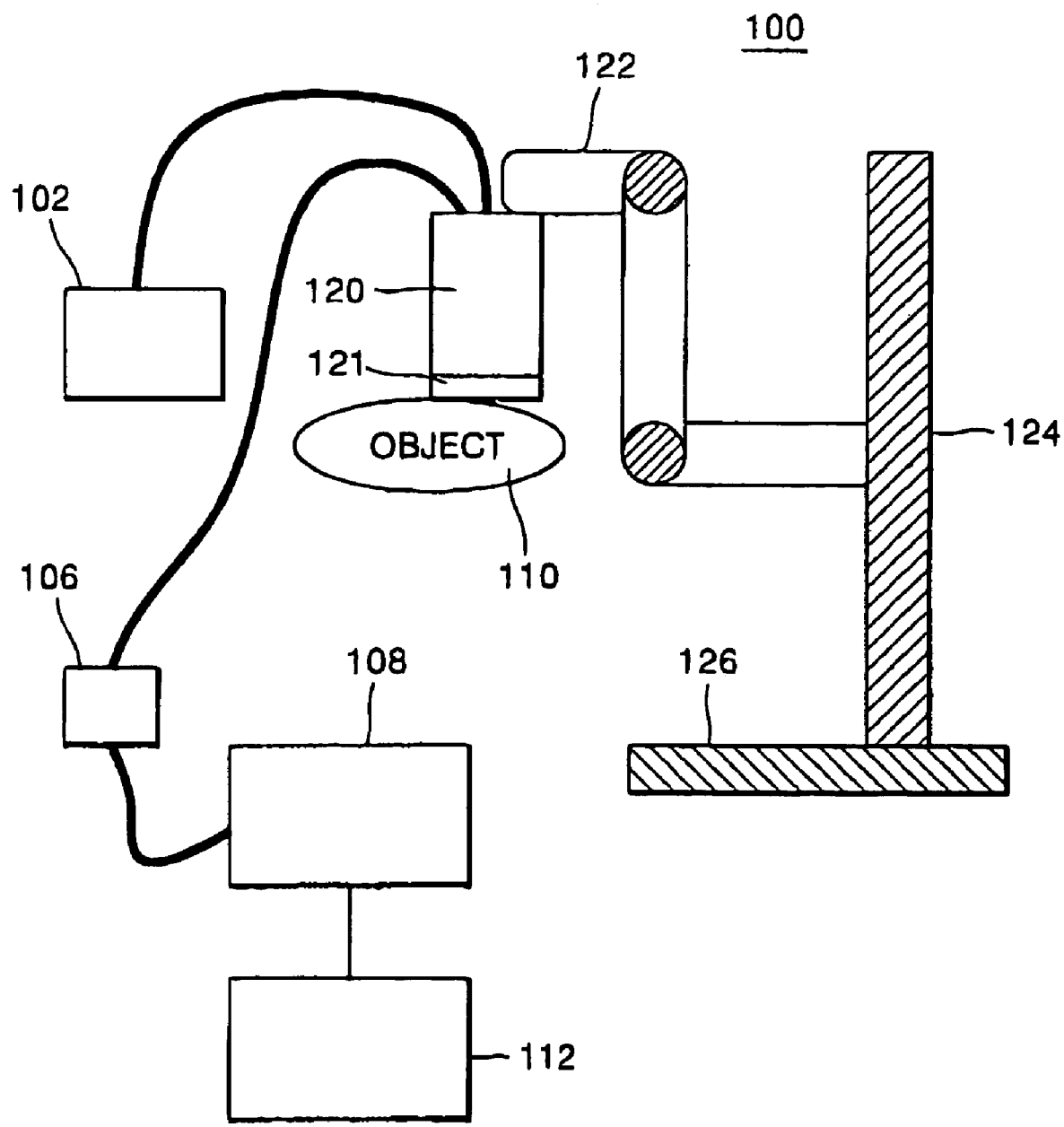
FIG. 1 illustrates a device for measuring blood flow using bio-photon emission according to an embodiment of the present invention.

FIG. 1 illustrates a device for measuring blood flow using bio-photon emission according to an embodiment of the present invention.

Referring to FIG. 1, a blood flow measurement device 100 includes a power supply 102, a detector 120, which may be a photomultiplier (PMT) or an optical receiver, a preamplifier 106, a processor 108, such as a computer/counting board, which may include a display, and a conveyor including a convey arm 122, a support 124, and a stand 126. In operation, the power supply 102 supplies power to the blood flow measurement device 100. The PMT 120 measures a bio-photon emission generated from an object 110. The preamplifier 106 converts the measured bio-photon emission into an electric signal and amplifies the electric signal. The processor 108 calculates the bio-photon emission using the amplified electric signal from the preamplifier 106. The convey arm 122 moves the detector 120, and the support 124 supports the convey arm 122. A shutter 121 is attached to the detector 120 to control an amount of light that is incident on the detector 120.

In the present embodiment, the detector 120 is three-dimensionally movable. By controlling the detector 120 using the convey arm 122, which is attached to the support 124 fixed to the stand 126, the detector 120 may be positioned adjacent to the object 110, i.e., a living body such as a human body. In the context of the present invention, adjacent may mean in contact with or in close proximity.

Thereafter, the shutter 121 attached to the detector 120, which has been previously turned on, is opened. The shutter 121 remains closed until measurement begins because the detector 120 is susceptible to damage caused by exposure to light.

The detector 120 is able to measure the bio-photon emission, which is much dimmer than starlight. It is impossible to measure the bio-photon emission using a typical method of measuring light. The bio-photon emission may be measured in a darkroom.

The present invention is based on an assumption that the bio-photon emission varies with a state of the human body. In an embodiment of the present invention using a photomultiplier (PMT) as the detector, since the PMT, which typically measures a bio-photon emission of a solid, amplifies one photon by a factor of a million to allow the bio-photon emission to be measured, the PMT should be manufactured to measure ultrafaint light. The PMT is able to measure an amount of light radiated by a single bio-photon and thus, it can be referred to as a single photon counting.

The bio-photon emission measured by the detector 120 is displayed by the processor 108 through the preamplifier 106 so that a user is informed of a measurement result in real time. The preamplifier 106 converts the bio-photon emission measured by the detector 120 into an electric signal, or a voltage, amplifies the electric signal, and outputs the amplified electric signal to the processor 108.

In an embodiment of the present invention, measurement of the bio-photon emission may be performed for about thirty (30) seconds after a dark level is measured.

In an embodiment of the present invention, the device may further include a communication device 112. The communication device 112 is capable of transmitting results of the analysis of the bio-photon emission, thereby enabling remote treatment and accumulation of information on the health states of individuals.

When an experiment was conducted according to an embodiment of the present invention, a relationship between blood pressure and the measured bio-photon emission was identified as shown in the Table 1.

TABLE 1

| Blood pressure | Bio-photon emission |
| --- | --- |
| 60 | 200 |
| 70 | 170 |
| 80 | 150 |
| 110 | 140 |

Referring to Table 1, it may be seen that as the blood pressure increases, the bio-photon emission decreases. Accordingly, when the blood flow measurement device 100 is used, it is possible to measure the bio-photon emission generated from a living body and predict a state of blood flow based on the measured bio-photon emission, thereby facilitating diagnosis of a health state of the living body.

Figure 2:
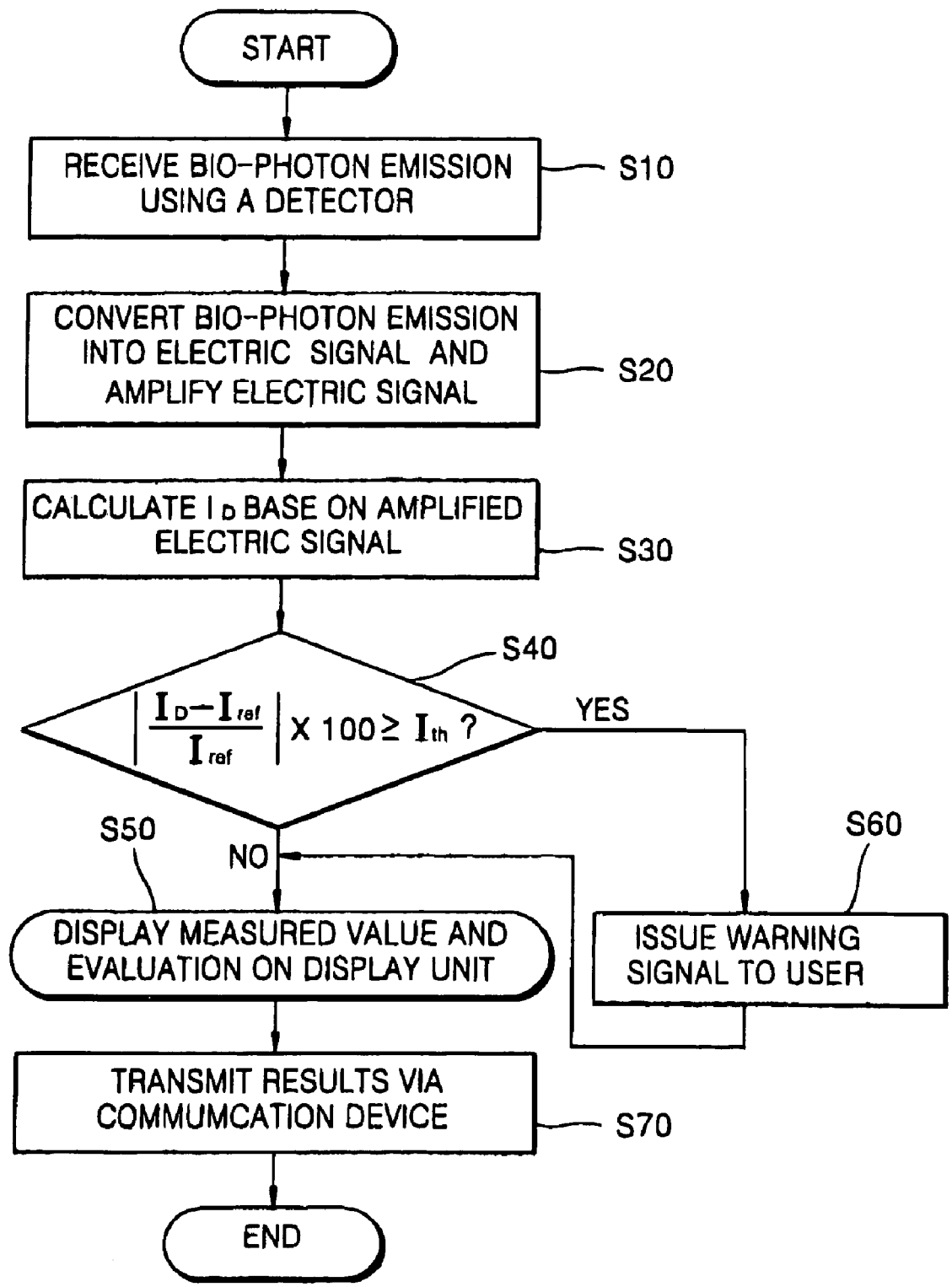
FIG. 2 is a flowchart illustrating a method of measuring blood flow using bio-photon emission according to an embodiment of the present invention.

FIG. 2 is a flowchart illustrating a method of measuring blood flow using bio-photon emission, the method being performed in the device of FIG. 1.

Hereinafter, the method shown in FIG. 2 will be described with reference to the blood flow measurement device 100 shown in FIG. 1.

In operation S10, a user positions the detector 120 adjacent to an object 110, i.e., a living body, by controlling the convey arm 122 and opens the shutter 121, thereby allowing the detector 120 to receive bio-photon emission.

In operation S20, the bio-photon emission received by the detector 120 is converted into an electric signal, which is amplified by the preamplifier 106, and then output to the processor 108.

In operation S30, an amount $I_D$ of bio-photon emission measured per unit of time is calculated by the processor 108 based on the amplified electric signal.

Next, in operation S40, a presence of a disorder of the living body may be determined using the following inequality:

$$\left|\frac{I_D - I_{ref}}{I_{ref}}\right| \times 100 \geq I_{th} \quad (1)$$

wherein $I_{ref}$ is an average of the amounts of bio-photon emissions that have been measured from the living body for several days before the present measurement, and $I_{th}$ is a preset critical value. If $I_{th}$ is preset to 20, when the measured $I_D$ is greater than +20% or less than −20%, the calculated value, $$\left|\frac{I_D - I_{ref}}{I_{ref}}\right| \times 100,$$

exceeds the critical value $I_{th}$.

If, in operation S40, it is determined that the calculated value is equal to or less than the critical value $I_{th}$, then, in operation S50, measured data and evaluation thereof can be displayed on a display unit (not shown), for example, a liquid crystal display (LCD).

If, however, in operation S40, it is determined that the calculated value exceeds the critical value $I_{th}$, then, in operation S60, a warning signal, such as a beep, is sent to the user and measured data and evaluation thereof are displayed on the display unit. The evaluation may include a notice of a blood flow abnormality along with an analysis of the associated disorder.

The method may additionally include, in operation S70, transmitting results of the analysis of the bio-photon emission via the communication device 112.

As described above, the present invention provides information on blood flow by using bio-photon emission, which varies with a state of a human body, as a bio signal without having to apply any physical, chemical, or physiological stimulus to the human body.

In comparison with conventional blood flowmeters, which are time-consuming to use and thus, incur significant cost, the method and device of an embodiment of the present invention are economical and relatively simple.

Also, the present invention enables real time measurement so that a patient being examined may be instantaneously informed of the results and promptly take necessary measures based on the measurement results.

Further, since the bio-photon emission is converted into an electric signal, the device of the present invention can be directly connected to various communication devices, thereby enabling remote treatment and accumulation of information on the health states of individuals.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A device for measuring blood flow of a living body having blood vessels that emit bio-photons and through which blood flows, the device comprising:
   a detector adapted to be positioned adjacent to a predetermined portion of the living body for measuring a bio-photon emission from the living body; and
   a processor for analyzing and displaying the blood flow of the living body based on a value of the bio-photon emission, wherein the processor calculates the amount of bio-photon emission measured per unit of time and predicts a state of blood flow based on the measured bio-photon emission, with decreasing bio-photon emissions correlating to increasing blood pressure.

2. The device as claimed in claim 1, further comprising a shutter for controlling an amount of light incident on the detector.

3. The device as claimed in claim 1, wherein the detector operates in a darkroom.

4. The device as claimed in claim 1, wherein the detector is a photomultiplier or an optical receiver.

5. The device as claimed in claim 1, further comprising:
   a power supply for supplying power to the detector;
   a conveyor operable to move the detector three-dimensionally; and
   a preamplifier for converting the bio-photon emission detected by the detector into an electric signal and amplifying the electric signal.

6. The device as claimed in claim 5, wherein the conveyor comprises:
   a stand;
   a support fixed on the stand; and
   a convey arm attached to the support operable to three-dimensionally control the movement of the detector.

7. The device as claimed in claim 1, wherein the processor comprises a display unit.

8. The device as claimed in claim 1, further comprising a communication device for transmitting results of the analysis of the bio-photon emission.

* * * * *